(12) United States Patent
Lawrynowicz et al.

(10) Patent No.: US 8,187,660 B2
(45) Date of Patent: May 29, 2012

(54) METHOD FOR FABRICATING A MEDICAL IMPLANT COMPONENT AND SUCH COMPONENT

(75) Inventors: Daniel E. Lawrynowicz, Cornwall, NY (US); Aiguo Wang, Wayne, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1417 days.

(21) Appl. No.: 11/325,841

(22) Filed: Jan. 5, 2006

(65) Prior Publication Data

US 2007/0154620 A1 Jul. 5, 2007

(51) Int. Cl.
*A61F 2/28* (2006.01)
*A61F 2/30* (2006.01)
*B05D 3/02* (2006.01)
*B05D 1/02* (2006.01)
*B05D 1/08* (2006.01)
*B22F 3/10* (2006.01)

(52) U.S. Cl. ...... 427/2.24; 427/2.26; 427/2.27; 427/4.21; 427/372.2; 623/16.11; 623/18.11; 623/23.56; 623/23.6

(58) Field of Classification Search .......... 427/2.1–2.31, 427/421.1, 372.2; 623/11.11, 18.11–23.46
See application file for complete search history.

(56) References Cited

U.S. PATENT DOCUMENTS

| | | |
|---|---|---|
| 3,707,006 A | 12/1972 | Bokros et al. |
| 4,131,459 A | 12/1978 | Fletcher et al. |
| 4,145,764 A | 3/1979 | Suzuki et al. |
| 4,309,488 A | 1/1982 | Heide et al. |
| 4,957,509 A * | 9/1990 | Tamari et al. .......... 424/423 |
| 5,258,030 A | 11/1993 | Wolfarth et al. |
| 5,330,826 A * | 7/1994 | Taylor et al. .......... 428/216 |
| 5,370,694 A | 12/1994 | Davidson |
| 5,370,696 A | 12/1994 | Jamison et al. |
| 5,405,389 A | 4/1995 | Conta et al. |
| 5,441,537 A | 8/1995 | Kenna |
| 5,480,438 A | 1/1996 | Arima et al. |
| 5,489,306 A | 2/1996 | Gorski |
| 5,674,293 A * | 10/1997 | Armini et al. .......... 623/23.36 |
| 5,728,637 A * | 3/1998 | Mishra et al. .......... 501/127 |

(Continued)

FOREIGN PATENT DOCUMENTS

DE 39 14 999 9/1990

(Continued)

OTHER PUBLICATIONS

Office Action from corresponding Canadian Application, 2,572,699, dated Sep. 10, 2008.

*Primary Examiner* — Timothy Meeks
*Assistant Examiner* — Cachet Sellman
(74) *Attorney, Agent, or Firm* — Lerner, David, Littenberg, Krumholz & Mentlik, LLP

(57) ABSTRACT

A method of fabricating a medical implant component. The method may include the steps of producing a substrate from a first material wherein the substrate has a bearing portion, spraying particles of a second material onto the bearing portion in accordance with a predetermined spraying technique to provide a coating thereon, and subjecting the coated bearing portion to a hot isostatic pressing process, a vacuum sintering process, or a controlled atmospheric sintering process. The first material may be the same as or different from the second material. The predetermined spraying technique may be a thermal type spraying process such as a plasma spraying process or a high velocity oxygen fuel spraying process.

28 Claims, 5 Drawing Sheets

U.S. PATENT DOCUMENTS

| | | | |
|---|---|---|---|
| 5,795,626 A | 8/1998 | Gabel et al. | |
| 5,807,407 A | 9/1998 | England et al. | |
| 5,868,796 A | 2/1999 | Buechel et al. | |
| 5,868,879 A | 2/1999 | Amick et al. | |
| 5,894,501 A * | 4/1999 | Doerr et al. | 376/409 |
| 5,910,170 A | 6/1999 | Reimink et al. | |
| 6,001,426 A | 12/1999 | Witherspoon et al. | |
| 6,026,316 A | 2/2000 | Kucharczyk et al. | |
| 6,074,135 A | 6/2000 | Tapphorn et al. | |
| 6,290,726 B1 * | 9/2001 | Pope et al. | 623/22.15 |
| 6,402,787 B1 | 6/2002 | Pope et al. | |
| 6,419,708 B1 | 7/2002 | Hall et al. | |
| 6,425,922 B1 | 7/2002 | Pope et al. | |
| 6,488,715 B1 | 12/2002 | Pope et al. | |
| 6,573,210 B1 | 6/2003 | Claussen et al. | |
| 6,582,470 B1 | 6/2003 | Lee et al. | |
| 6,652,588 B2 | 11/2003 | Hayes, Jr. et al. | |
| 6,715,640 B2 | 4/2004 | Tapphorn et al. | |
| 6,881,229 B2 | 4/2005 | Khandkar et al. | |
| 6,915,964 B2 | 7/2005 | Tapphorn et al. | |
| 7,163,715 B1 * | 1/2007 | Kramer | 427/189 |
| 7,678,325 B2 * | 3/2010 | Gardinier | 264/604 |
| 2002/0052659 A1 | 5/2002 | Hayes et al. | |
| 2002/0111694 A1 | 8/2002 | Ellingsen et al. | |
| 2002/0168466 A1 | 11/2002 | Tapphorn et al. | |
| 2003/0045941 A1 | 3/2003 | Lewallen | |
| 2003/0050705 A1 * | 3/2003 | Cueille et al. | 623/22.24 |
| 2003/0171820 A1 | 9/2003 | Wilshaw et al. | |
| 2003/0220699 A1 | 11/2003 | Hunter et al. | |
| 2004/0002766 A1 | 1/2004 | Hunter et al. | |
| 2004/0026030 A1 | 2/2004 | Hatono et al. | |
| 2004/0043230 A1 | 3/2004 | Hatono et al. | |
| 2004/0111159 A1 | 6/2004 | Pope et al. | |
| 2004/0126566 A1 | 7/2004 | Axen et al. | |
| 2004/0133283 A1 * | 7/2004 | Shetty | 623/23.55 |
| 2004/0153165 A1 | 8/2004 | Li et al. | |
| 2004/0158330 A1 | 8/2004 | Muller et al. | |
| 2004/0247903 A1 | 12/2004 | Axen et al. | |
| 2004/0267371 A1 | 12/2004 | Hayes et al. | |
| 2005/0049716 A1 | 3/2005 | Wagener et al. | |
| 2005/0072601 A1 | 4/2005 | Griffo et al. | |
| 2005/0084701 A1 | 4/2005 | Slattery | |
| 2005/0102034 A1 | 5/2005 | Hayes et al. | |
| 2005/0102035 A1 | 5/2005 | Grundei | |
| 2005/0107870 A1 | 5/2005 | Wang et al. | |
| 2005/0123672 A1 | 6/2005 | Justin et al. | |
| 2005/0203630 A1 | 9/2005 | Pope et al. | |
| 2006/0085079 A1 | 4/2006 | Carroll | |
| 2006/0184251 A1 * | 8/2006 | Zhang et al. | 623/23.56 |
| 2008/0275568 A1 * | 11/2008 | Shikata et al. | 623/23.56 |

FOREIGN PATENT DOCUMENTS

| | | |
|---|---|---|
| DE | 39 28 845 | 3/1991 |
| EP | 1 679 088 | 7/2006 |
| GB | 2397765 | 8/2004 |
| WO | 89/05161 | 6/1989 |
| WO | 2004/002544 | 1/2004 |
| WO | 2004/071350 | 8/2004 |
| WO | 2006/033956 | 3/2006 |

* cited by examiner

As-SPRAYED

Ti SUBSTRATE    NANOCERAMIC COATING

AFTER HIP PROCESS

Ti SUBSTRATE — 100    102  104  106  108

200 Ti SUBSTRATE    202  204  206    208

METHOD FOR FABRICATING A MEDICAL IMPLANT COMPONENT AND SUCH COMPONENT

CROSS-REFERENCE TO RELATED APPLICATIONS

N/A

FIELD OF INVENTION

The present invention relates to a method of fabricating a medical implant component having a bearing surface and to such medical implant component and, more particularly, to such method and component wherein the bearing surface is formed by spraying particles of a desired material onto a bearing portion of a substrate.

BACKGROUND OF THE INVENTION

Medical implant components may be used within a patient for replacement surgery such as hip replacement surgery or the like. Such medical implant components may include femoral head components and acetabular cup components. With such components, a ball portion of the femoral head component is adapted to mate with a bearing portion of the acetabular cup component.

To provide an acceptable mating condition, the ball portion may be coated with a coating material. Typically, such coating may be applied by a chemical vapor deposition (CVD) process or a physical vapor deposition (PVD) process. These coating processes may enable only a relatively thin coating to be applied. That is, the maximum thickness typically attainable by either of these processes is approximately 20 microns.

The use of a relatively thin coating (e.g., 20 microns or less) on a bearing surface of a medical implant component may result in a failure of the coating during actually use. As an example, consider the situation if a foreign material were to get into the joint between the ball portion of the femoral head component and the bearing portion of the acetabular cup component. During movement, the foreign material may rub against the coating on the ball portion. As a result, a scratch or crack in the coating may develop which may spread into a larger crack. Additionally, other scratches or cracks may also develop and grow into larger cracks. Eventually, such crack or cracks may result in particles of the coating material being removed from or flaking off from such coating material. As is to be appreciated, such particles or flakes of the coating material inside a patient are not desirable.

In addition to above, there may be a number of other disadvantages associated with merely the use of a CVD or a PVD process or technique to coat a bearing surface of a medical implant component. For example, heat treating may not be performed after such coating is applied. As a result, there may not be any diffusion or substantially no diffusion of the coating material into the substrate material. In other words, in such situation, there may be a distinct boundary between the coating and the substrate of the medical implant component.

Additionally, the above-described techniques may produce a bearing surface which does not have a relatively hard surface. As a result, to minimize wear, the material of the mating implant component may be a relatively soft material or may have a relatively low hardness value.

Furthermore, the above-described techniques may be usable only with relatively simple shapes.

As such, it would be advantageous to provide a technique for applying a coating to a bearing portion of a component, such as a medical implant component, which would enable such coating to be relatively thick and/or to have a relatively hard surface and/or to be inter-diffused with the material of the substrate so as to improve the wear performance of such component. It would also be advantageous to provide such technique which may be usable with components having non-simple geometries or shapes.

SUMMARY OF THE INVENTION

In accordance with an aspect of the present invention, a method of fabricating a medical implant component is provided. Such method may comprise the steps of producing a substrate from a first material in which the substrate has a bearing portion, spraying particles of a second material onto the bearing portion of the substrate in accordance with a predetermined spraying technique to provide a coating thereon, and subjecting the coated bearing portion to a hot isostatic pressing process, a vacuum sintering process, or a controlled atmospheric sintering process. Upon completion of the fabrication, the bearing portion is a bearing surface which is operable to articulate with a portion of a member or another medical implant component.

The predetermined spraying technique may be a thermal type spraying process, such as one of a plasma spraying process or a high velocity oxygen fuel (HVOF) spraying process.

The first material may be the same as the second material; alternatively, the first material may be different from the second material. For example, the first material may be a biocompatible metal or an alloy thereof; and, the second material may be a ceramic material or a ceramic metal (cermet) composite material, in which the ceramic material may be any one of an oxide, carbide, nitride, or nitro-carbide of any of the following elements: silicon (Si), titanium (Ti), tantalum (Ta), tungsten (W), zirconium (Zr), niobium (Nb), chromium (Cr), or aluminium (Al), and the cermet composite material may be formed from any (i) oxide, carbide, nitride, or nitro-carbide of any of the following elements: Si, Ti, Ta, W, Zr, Nb, Cr, or Al, and (ii) any of Ti or an alloy thereof, cobalt chrome or an alloy thereof, Zr metal or an alloy thereof, Ta or an alloy thereof, or stainless steel.

In accordance with another aspect of the present invention, a method of fabricating a medical implant component is provided which may comprise the steps of producing a substrate from a first material in which the substrate has a bearing portion, spraying particles of a second material onto the bearing portion of the substrate in accordance with a predetermined spraying technique to provide a coating of the second material thereon having a first thickness, grinding the coating of the second material so that the coating has a second thickness which is less than the first thickness, and subjecting the coating of the second material after the coating has been ground to the second thickness to a hot isostatic pressing process, a vacuum sintering process, or a controlled atmospheric sintering process. Upon completion of the fabrication, the bearing portion of the substrate having the coating of the second material is operable to articulate with a portion of a member or another medical implant component.

Such method may further comprise the step of grinding the coating of the second material after the substrate has been subjected to the hot isostatic pressing process, vacuum sintering process, or controlled atmospheric sintering process so that the coating has a third thickness which is less than the second thickness.

The predetermined spraying technique may be a thermal type spraying process, such as a plasma spraying process or a high velocity oxygen fuel (HVOF) spraying process.

The first material may be the same as the second material; alternatively, the first material may be different from the second material. For example, the first material may be a biocompatible metal or an alloy thereof, and the second material may be a ceramic material such as chromium oxide or chromium carbide.

In accordance with yet another aspect of the present invention, a medical implant component is provided. Such medical implant component may comprise a substrate fabricated from a first material and including a bearing portion having a coating of a second material thereon so as to form a bearing surface operable to articulate with a portion of a member or another medical implant component, in which the coating has a thickness of at least approximately 25 microns, and in which an interface between the substrate and the coating is an interdiffusion zone of the first material and the second material.

The first material may be the same as the second desired material; alternatively, the first desired material may be different from the second material. For example, the first material may be a biocompatible metal or an alloy thereof, and the second material may be a ceramic material or a ceramic metal (cermet) composite material. Such ceramic material may be any one of an oxide, carbide, nitride, or nitro-carbide of any of the following elements: silicon (Si), titanium (Ti), tantalum (Ta), tungsten (W), zirconium (Zr), niobium (Nb), chromium (Cr), or aluminium (Al); and the cermet composite material may be formed from any (i) oxide, carbide, nitride, or nitrocarbide of any of the following elements: Si, Ti, Ta, W, Zr, Nb, Cr, or Al, and (ii) any of Ti or an alloy thereof, cobalt chrome or an alloy thereof, Zr metal or an alloy thereof, Ta or an alloy thereof, or stainless steel.

BRIEF DESCRIPTION OF THE DRAWINGS

A more complete appreciation of the subject matter of the present invention and the various advantages thereof can be realized by reference to the following detailed description in which reference is made to the accompanying drawings wherein like reference numbers or characters refer to similar elements.

DETAILED DESCRIPTION OF THE PREFERRED EMBODIMENTS

Figure 1:
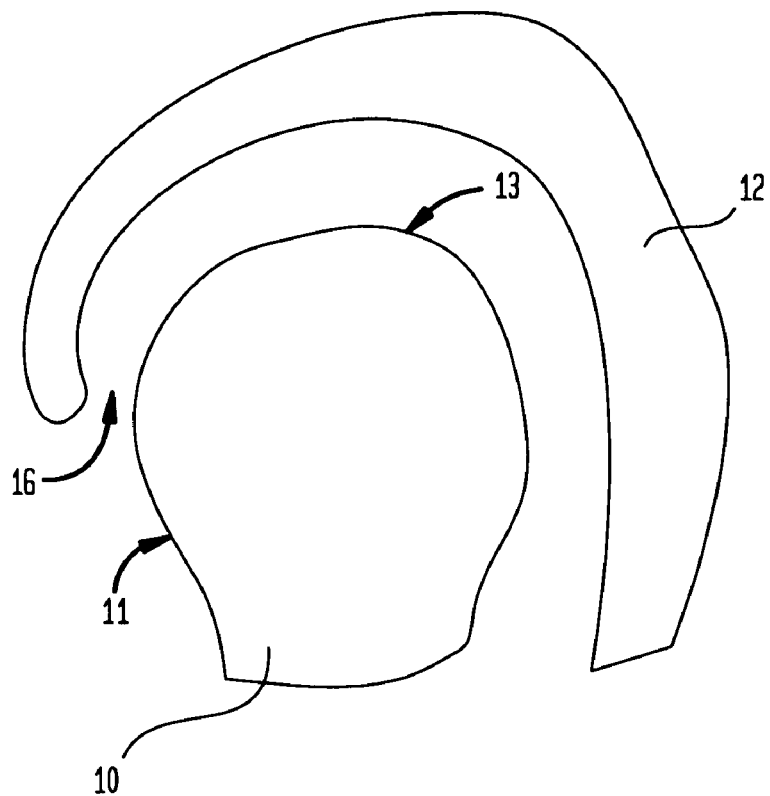
FIG. 1 is a diagram of two medical implant components which are adapted to mate together.

The present invention may be applied to a medical implant component and, in particular, to such component having a so-called bearing surface. As an example, reference is made to FIG. 1 which illustrates a femoral head 10 and an acetabular cup 12 which may be used in hip replacement surgery. Such femoral head 10 may be adapted to be inserted into the acetabular cup 12 when surgically placed within a patient. More particularly, during such placement, a bearing surface 13 of a ball portion 11 of the femoral head 10 may be inserted into a mating or insert portion 16 of the acetabular cup 12. To provide an acceptable mating condition, the bearing surface 13 may have had a coating material applied thereto, as herein below more fully described.

Figure 2:
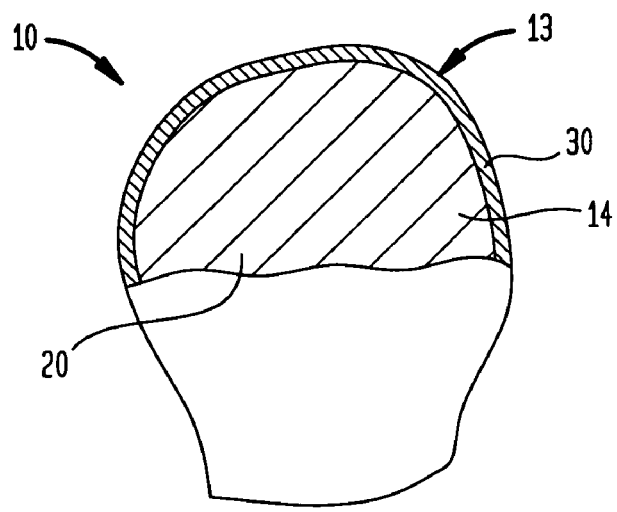
FIG. 2 is a diagram of a medical implant component in accordance with an embodiment of the present invention.

FIG. 2 illustrates a partial cross-section of a medical implant component, such as the femoral head 10, in accordance with an aspect of the present invention. As shown therein, such component may include a coating 30 which has been applied to the outer surface or bearing portion 14 of a substrate 20 of the femoral head 10. It should be noted that at least a portion of the outer surface of the coating layer 30, after all processing thereon is completed, may be considered to be the bearing surface 13.

The coating 30 may be applied to the bearing portion 14 by a spraying process. Such spraying process may be a thermal type spraying process, such as a plasma spraying process or a high velocity oxygen fuel (HVOF) spraying process. The HVOF spraying process may be a gas fuel process such as a propane type process or, alternatively, may be a liquid fuel process such as a kerosene type process. Additionally, such spraying process may be performed by a so-called high velocity cold spraying process such as that described in co-pending application entitled "High Velocity Spray Technique for Medical Implant Components" with inventors Daniel E. Lawrynowicz, Aiguo Wang, and Eric Jones and having application Ser. No. 11/325,790, filed Jan. 5, 2006, which is hereby incorporated by reference.

The spraying process may be controlled or regulated such that a predetermined amount of coating material is applied to the substrate during a predetermined time interval or during each pass. More specifically, the spraying operation may be performed in an apparatus having a fixture for holding the medical implant component and a spray gun or nozzle from which the coating or spray material is supplied. During the spraying operation, either or both of the spray gun and/or fixture may move in a predetermined or controlled manner. For example, the fixture having the medical implant component may rotate at a predetermined rate in front of the spray gun. As a result, the amount of coating material which is applied to the substrate of the medical implant component during each revolution or pass may be controlled to a predetermined value. For example, such control may result in a thickness of coating material of approximately 10 to 12.5 microns or less being applied in each pass.

The material used for the coating 30 may be same material as that of the substrate 20 of the femoral head 10. Alternatively, such coating material may be different from the material of the substrate 20. For example, the substrate may be formed from any biocompatible metal or an alloy thereof such as cobalt chromium (CoCr) or an alloy thereof, titanium (Ti) or an alloy thereof, zirconium (Zr) or an alloy thereof, tantalum (Ta) or an alloy thereof, niobium (Nb) or an alloy thereof, or stainless steel; and the coating material may be a ceramic type material or a so-called cermet (or ceramic metal composite) type material. For instance, the ceramic type material may be an oxide, carbide, nitride, or nitro-carbide of any of the following elements: silicon (Si), titanium (Ti), tantalum (Ta), tungsten (W), zirconium (Zr), niobium (Nb), chromium (Cr), and aluminium (Al); and the cermet type material may be any of the previously mentioned materials and Ti and its alloys, cobalt chrome and its alloys, Zr metal and its alloys, stainless steel, and Ta and its alloys. Furthermore, alloying metals, such as silver (Ag), may be added to the metal for the substrate so as to enhance certain properties thereof.

A number of parameters or factors may influence which coating material is to be used. Such parameters may include the difference between the thermal coefficient of expansion (TCE) of the coating material and that of the substrate, the desired thickness of the coating, the desired density or hardness of the coating, and/or the geometry of the component (e.g., the radius of curvature of the bearing surface thereof). From these parameters, a number of relationships may exist. For example, the larger the mismatch in the thermal coefficients of expansion between the coating material and the substrate, the thinner the coating; the smaller the radius of curvature of the bearing portion of the medical component, the closer the thermal coefficients of expansion and/or the thinner the coating; and/or the higher the desired density or hardness, the closer the thermal coefficients of expansion and/or the thinner the coating.

Consideration of the above-described parameters and/or relationships may be helpful in view of the heat treating operation, herein below more fully described.

Furthermore, if the difference in the thermal coefficient of expansion of the coating and that of the substrate or metal is less than a predetermined value and/or if the thickness of the coating applied in each pass is less than another predetermined value, then a coating of any reasonable thickness may be applied to almost any shaped surface. For example, if the difference between the thermal coefficient of expansion of the coating material ($TCE_c$) and the thermal coefficient of expansion of the substrate or metal ($TCE_m$) is less than approximately $1.0 \times 10^{-6}$/C, (where C is degrees Centigrade) and if the thickness of coating applied in each pass is less than approximately 10 microns, then a coating of any reasonable thickness (such as between 100 and 500 microns) may be applied to the bearing portion 14 of the femoral head 10. In fact, under such conditions, a coating having a substantially thicker value (such as up to 0.25 of an inch or more) may be applied to a bearing portion of a component, such as to the bearing portion 14 of the femoral head 10.

Accordingly, the spraying operation may enable a coating to be applied to a bearing portion of a component with a thickness of 100 to 500 microns, or even thicker.

After the coating is applied to the bearing portion 14, it may be subjected to a predetermined thermal consolidation or heat treating process. Such process may be utilized to create an inter-diffusion region between the coating and the substrate, as herein below more fully described. Such process may be a so-called hot isostatic pressing (HIPing) process, a so-called vacuum sintering process, or a so-called controlled atmospheric sintering process.

Figure 3A:
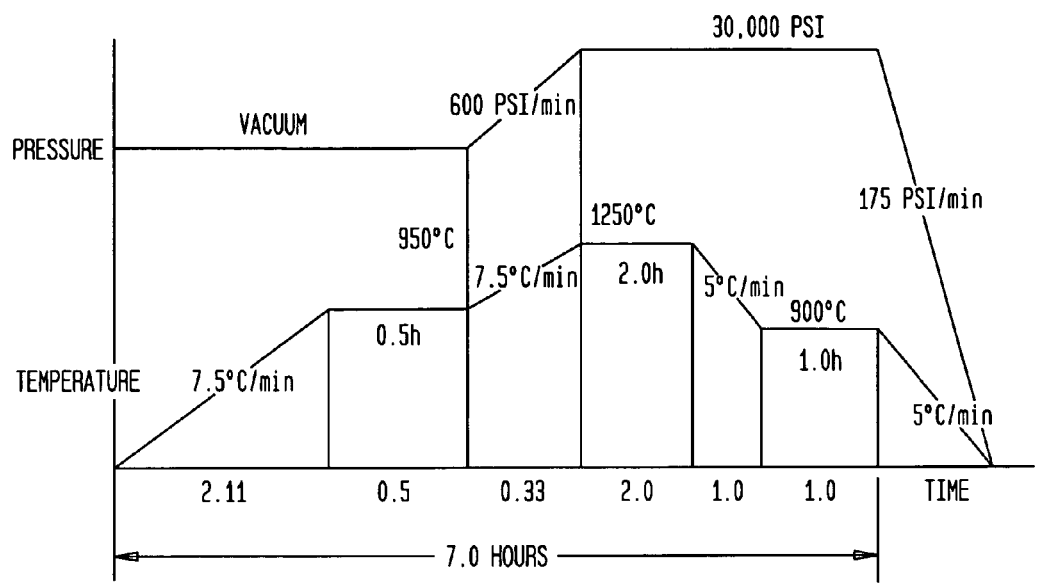
FIGS. 3a, 3b, and 3c are diagrams of profiles.

Hot isostatic pressing (HIPing) may be performed at relatively high temperatures and/or pressures using a gas such as argon or helium. As an example, FIG. 3a illustrates a profile which may be utilized for a HIPing process for the femoral head 10 having a coating applied to its bearing portion. During such HIPing process, the temperature and the pressure may vary over time in the manner shown in FIG. 3a. The vacuum indicated in FIG. 3a may be a relatively low pressure, such as approximately $10^{-5}$ or $10^{-4}$ Torr. As is to be appreciated, the HIPing process may not be limited to the temperatures and/or pressures and/or profile provided in FIG. 3a, and, instead may be performed at other temperatures and/or pressures for different periods of time.

Figure 3B:
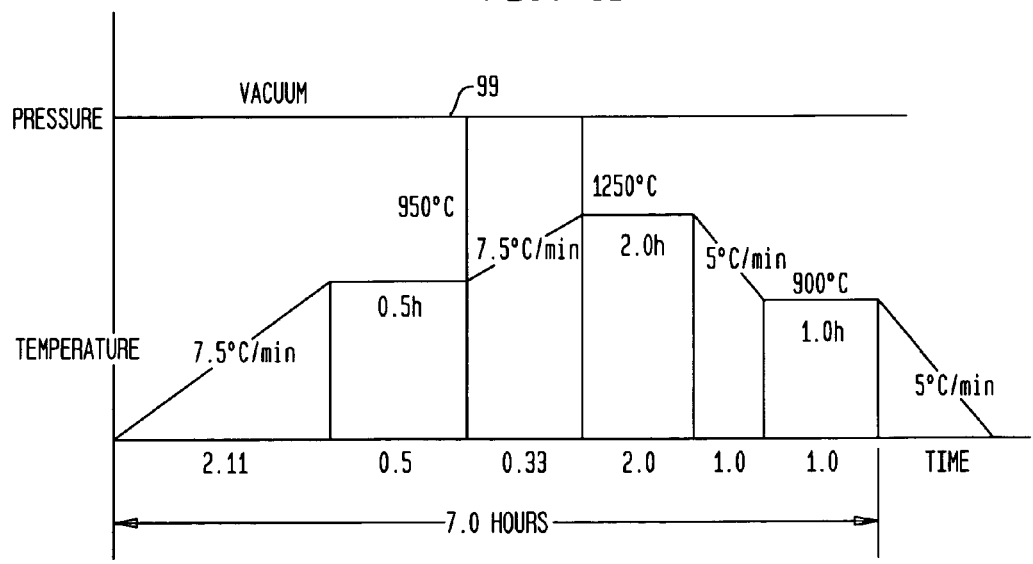

Pressureless or vacuum sintering may be performed under a vacuum or at a relatively low pressure or pressures. As an example, FIG. 3b illustrates a profile which may be utilized for a vacuum sintering process for the femoral head 10 having a coating applied to its bearing portion. In this situation, the pressure may be maintained at a constant or substantially constant value, such as that indicated by line 99. Such pressure value may be relatively low, such as approximately $10^{-5}$ Torr. The temperature profile for the vacuum sintering process may be as indicated in FIG. 3b. Further, the vacuum sintering process is not limited to the temperatures and/or pressure and/or profile provided in FIG. 3b, and, instead may be performed at other temperatures and/or pressure for different periods of time.

Figure 3C:
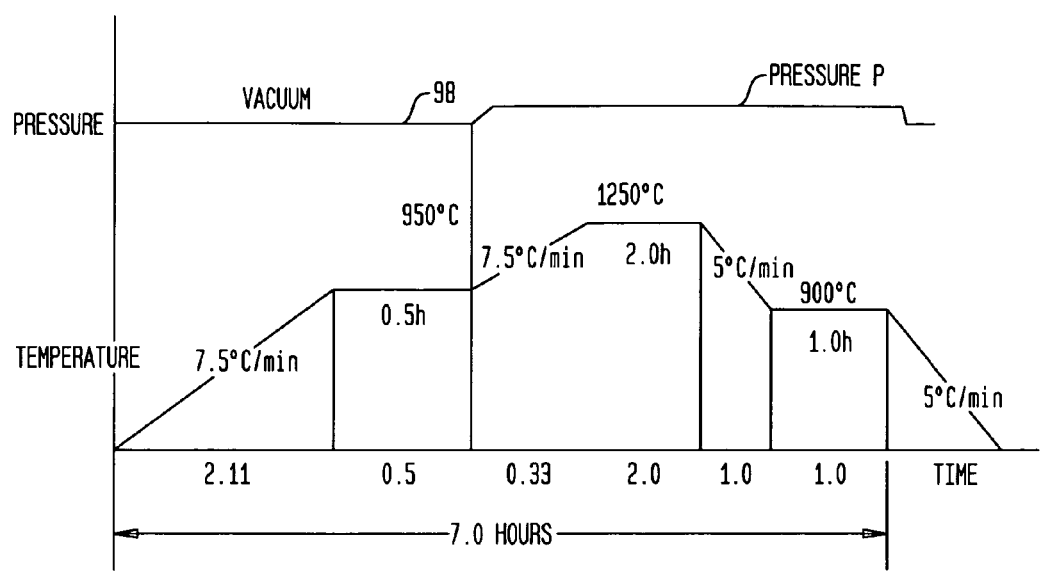

Controlled atmospheric sintering may be performed using a noble (or inert) gas, a reactive gas, or a mixture thereof. Examples of such gases may include argon, hydrogen, propane, krypton, carbon dioxide, carbon monoxide, and so forth. Additionally, the gas used in this process may consist entirely or substantially entirely of one of these gases or a blend which includes one of these gases. Furthermore, controlled atmospheric sintering may be performed in a controlled atmospheric setting, such as that created by using a partial pressure of a gas (such as argon). This process may also be considered a positive pressure controlled atmospheric sintering process. FIG. 3c illustrates an example of a profile which may be utilized for a controlled atmospheric sintering process for the femoral head 10 having a coating applied to its bearing portion. In this situation, a vacuum (or a relatively low pressure) may be maintained for a portion of the process, and then an inert gas (such as argon) may be added so that the pressure may be increased to a value P as indicated by line 98. The vacuum may have a relatively low pressure, such as approximately $10^{-4}$ or $10^{-5}$ Torr, and the pressure value P may have a low value which may be slightly higher, such as approximately $10^{-3}$ Torr. Argon may be backfilled into the chamber so that the entire chamber or substantially the entire chamber is filled with argon such that the pressure is equal to atmospheric pressure or above. The temperature profile for the controlled atmospheric sintering process may be as indicated in FIG. 3c. Further, the controlled atmospheric sintering process is not limited to the temperatures and/or pressures and/or profile provided in FIG. 3c, and, instead may be performed at other temperatures and/or pressures for different periods of time.

Generally, if the temperature during heat treating is increased, then the total time may be decreased; and, if the temperature during heat treating is decreased, then the total time may be increased. However, such general relationship may not always apply. For example, there may be a practical limit as to how low the temperature can be regardless of the length of time.

Each of the above-described heat treating processes may offer advantages. For example, and possibly depending on the materials utilized, the vacuum sintering process may result in a coating with a harder surface and lower density than that obtained from a sintering process in a reduced gas atmosphere, and the vacuum sintering process may produce a more homogeneous microstructure arrangement than that obtained from a so-called uniaxial hot pressing process in which pressure may be applied in one direction. Further, by performing the vacuum sintering process in a vacuum chamber, oxygen may be removed therefrom and, as a result, reactions involving oxygen (such as which may occur with a reactive material such as titanium when exposed to oxygen) may not occur. Furthermore, by performing such process in a vacuum chamber, undesirable contaminants may not be present. As another example, hot isostatic pressing (HIPing) may accomplish pressing and sintering in a single step, but may nevertheless be relatively expensive.

As a result of the thermal consolidation or heat treating process, the coating 30 may be diffused with the outer layer of the substrate 20. In other words, there may be an inter-diffusion between the coating 30 and the substrate 20 such that a distinct boundary between the coating and the substrate may not exist and instead a gradual change may exist between the materials thereof. That is, at the interface of the coating 30 and the substrate 20 there may be an inter-diffusion zone of the coating material and the substrate material. Further, the surface hardness may be increased after the heat treating process. For example, the surface hardness of the coating material may be only approximately 1100 to 1400 Vickers after the spraying operation, but may be increased to approximately 2000 to 2800 Vickers after the heat treating process. Furthermore, the porosity of the coating material may decrease after the heat treating process. For example, the porosity of the coating material may be approximately 3 to 5% after the spraying operation, but may be decreased to approximately 0 to 2% after the heat treating process.

An example of the above-described diffusion between the substrate and the coating will now be provided with reference to FIGS. 4a, 4b, 4c, and 5.

Figure 4A:
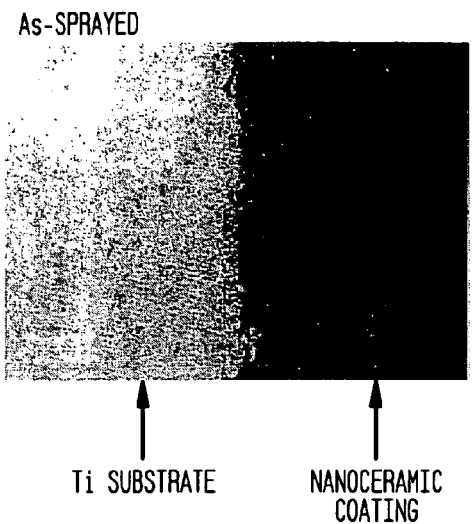
FIGS. 4a, 4b, and 4c are illustrations of a component having a coating layer which illustrate the component after being sprayed, after being subjected to a hot isostatic pressing process, and after being subjected to a vacuum sintering process, respectively.

FIG. 4a illustrates a photograph of a cross-section of a component having a substrate formed from titanium (Ti) and a nanoceramic coating of chrome oxide which has been sprayed onto the surface of the substrate. As clearly shown therein, there is a distinct boundary between the Ti substrate and the coating. In other words, there is no (or substantially no) diffusion between the substrate material and the coating material. Here, the coating may have only a mechanical bond with the substrate.

Figure 4B:
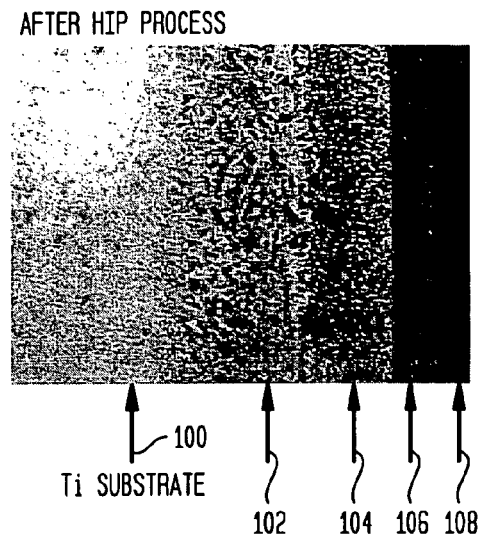

FIG. 4b illustrates the component of FIG. 4a after being subjected to a heat treating process (such as a HIPing process). As clearly shown therein, there is no longer a distinct boundary between the Ti substrate and the coating. Instead, there is an inter-diffusion between the substrate material and the coating material. More specifically, arrow 100 identifies a portion of the substrate which is all or substantially all titanium (Ti) and arrow 108 identifies a portion of the coating which is all or substantially all coating material (i.e., chrome oxide). The arrows in-between, that is, arrows 102, 104, and 106, identify portions which are partly Ti and partly chrome oxide. As is to be appreciated, arrow 102 identifies a portion which may include more Ti than chrome oxide, and arrow 106 identifies a portion which may include more chrome oxide than Ti, and arrow 104 identifies a portion which may include approximately the same amount of Ti and chrome oxide.

Figure 4C:
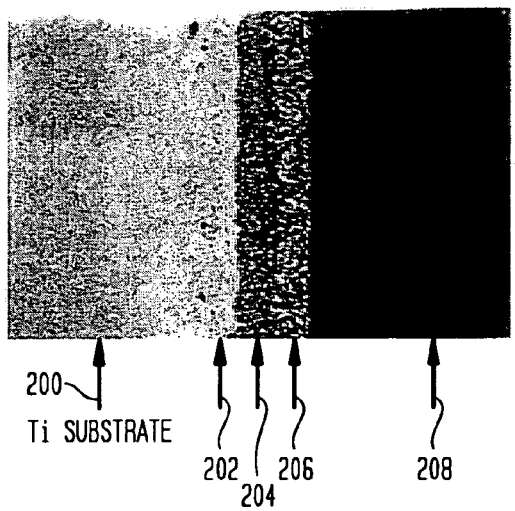

FIG. 4c illustrates the component of FIG. 4a after being subjected to a heat treating process (such as a vacuum sintering process). As clearly shown therein, and in a manner similar to that described above with regard to the HIPing process, there is no longer a distinct boundary between the Ti substrate and the coating. Instead, there is an inter-diffusion between the substrate material and the coating material. More specifically, arrow 200 identifies a portion of the substrate which is all or substantially all titanium (Ti) and arrow 208 identifies a portion of the coating which is all or substantially all coating material (i.e., chrome oxide). The arrows in-between, that is, arrows 202, 204, and 206, identify portions which are partly Ti and partly chrome oxide. As is to be appreciated, arrow 202 identifies a portion which may include more Ti than chrome oxide, and arrow 206 identifies a portion which may include more chrome oxide than Ti, and arrow 204 identifies a portion which may include approximately the same amount of Ti and chrome oxide.

Figure 5:
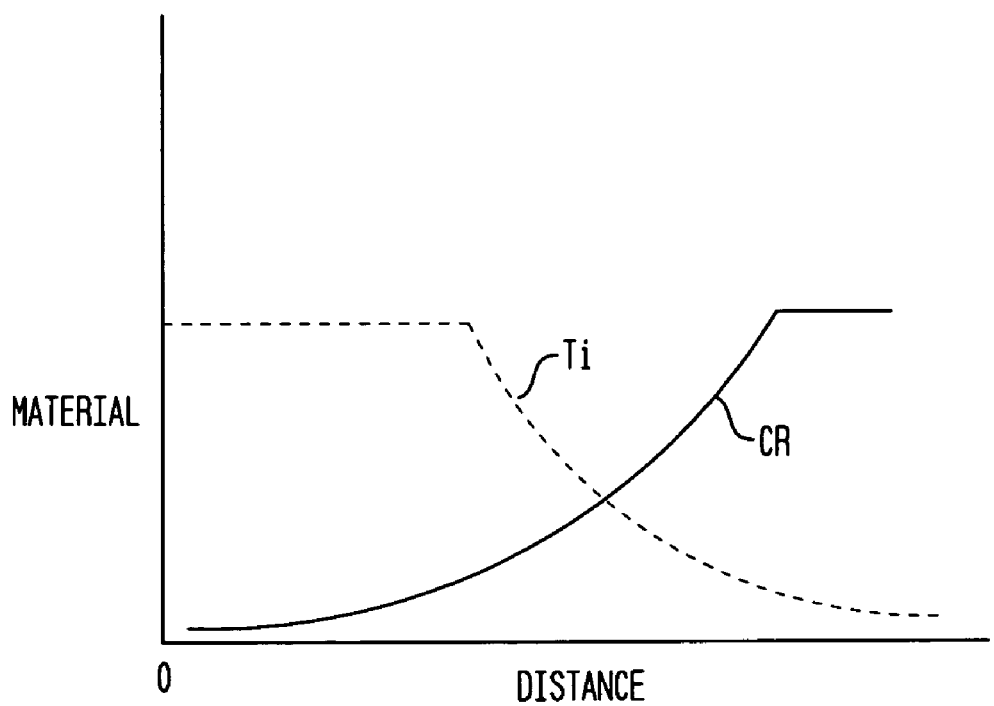
FIG. 5 is a graphical representation of the relationship of substrate material and coating material.

FIG. 5 illustrates a diagram of the relationship between the amount of the substrate material (Ti) and that of the coating material (chrome oxide) near and at the region where they meet after being subjected to one of HIPing process or a vacuum sintering process.

Thus, subjecting the component having a coating applied thereto to a thermal consolidation or heat treating process, such as one of those previously described, may result in the coating material having a diffusion or chemical bond with the substrate material.

The coating 30 may be machined or subjected to a grinding operation. Such grinding operation may be performed to remove a predetermined amount of the coating material and/or to provide a final desired size and/or to provide a desired surface roughness. Furthermore, the grinding operation may take place after the heat treating process. Alternatively, more than one grinding operation may be performed. For example, a first grinding operation may take place prior to the heat treating process and a second grinding operation may take place after the heat treating process. As an example of this latter situation, assume that a medical implant component (such as a femoral head) has a coating layer applied thereto in a manner such as that previously described and has a thickness of approximately 350 to 500 microns. Here, a first grinding operation may be performed prior to a heat treating process and may remove enough of the coating material so as to have a total coating thickness of approximately 100 to 200 microns. After the heat treating process, a second grinding (or polishing) operation may be performed so as to end up with the desired final overall size of the component and/or the desired surface roughness (Ra) With regard to the surface roughness, it may be desirable to have a predetermined finish such as a so-called mirror finish on the outer surface of the coating layer. In this regard, the surface roughness may have a value less than a predetermined value such as less than approximately 0.05 microns.

As an example of the above-described grinding operation (s), consider the situation wherein it is desired to end up with a component having a final outer diameter of 42 mm and a surface roughness (Ra) less than approximately 0.05 microns. In this situation, the component may be sprayed with the coating material so that its outer diameter is larger than 42 mm (e.g., 42.5 mm). Thereafter, the first or first and second grinding (or polishing) operations would remove enough of the coating material and/or polish the same such that the component would have a final outer diameter of 42 mm with a surface roughness of less than approximately 0.05 microns.

Thus, the coating layer may be subjected to one or more grinding or polishing operations so as to provide a desired final size and/or surface roughness. Although such grinding or polishing operation(s) may remove some of the coating material applied during the spraying operation, the final thickness of the coating material may still have a value equal to or greater than a predetermined value. Such predetermined value may be equal to approximately 25 microns.

Therefore, the minimum thickness of the final coating layer of the component (even if one or more grinding and/or polishing operations are performed) may be approximately 25 microns. However, it should be noted that such minimum thickness value could be substantially larger. In any event, such minimum thickness value is greater than the maximum thickness value which could be obtained from previously used processes for applying a coating layer to a bearing portion of a medical implant component (such as the previously described CVD process and PVD process).

By providing a relatively thick layer of a coating material on a bearing surface of a component (such as a medical implant component), and/or by subjecting the coating to a predetermined heat treating process, the present component has a coating with a relatively strong bond which may avoid coating problems or failures (such as cracking and/or flaking) that may occur in components having a relatively thin coating layer such as that applied by the previously used processes (e.g., the CVD or PVD process).

Thus, the present invention provides a technique whereby a coating may be applied to a component (such as a medical implant component) with substantially no upper limit on its thickness. Due to such relatively large thickness of the coating, the coating layer is less likely to wear or crack or have particles flake off as compared to thinner coatings. The use of heat treating may enable the coating to have a chemical or diffusion bond with the substrate and may provide a gradient therebetween wherein the hardness of the coating gradually merges into the substrate. Such bond may have a strength greater than that obtained by other techniques. For example, the bond strength for the present coating may be between approximately 7000-9000 psi, as compared to approximately 5000 psi obtained from other techniques. Further, the heat treating may also reduce the porosity of the coating and sinter unfused particles/boundaries which may lead to densification and significant increase in hardness. A mirror finish may be achievable after sufficient densification, which may be considered aesthetically pleasing. Furthermore, metal ion release may be reduced due to the improvement in corrosion resistance.

Moreover, the coating layer of the present invention may provide improved scratch resistance and wear resistance, as compared to the coating layers obtained by other techniques. Also, depending upon the materials used for the coating layer and the mating component, the coefficient of friction may be relatively low.

As is to be appreciated, although the present invention has been described for use with femoral head medical components, the present invention is not so limited. That is, the present invention may also be applied to other types of medical components and also to non-medical type components. For example, the present invention may be applied to other medical implant components having a bearing surface such as a femoral knee component (total, uni), a patella femoral bearing, a modular tibial baseplate or tray (top side to eliminate backside wear of polyethylene insert), a medical implant component for other joints (such as shoulder, ankle, elbow, finger, and so forth), a spinal implant (total disc replacement), and so forth. As another example, the present invention may be applied to a cardiovascular device, a stent, or other medical components. Additionally, the medical component having the coating may be adapted to mate with a mating member which is not another medical component. For example, the medical component having the coating may be adapted to mate with a portion of a bone, cartilage or the like within a patient.

Further, although in describing the present invention, the bearing portion of a femoral head component or the like was described as having a coating applied thereto, the present invention is not so limited. That is, the mating or insert portion of the mating component (such as an acetabular cup) may be coated with a coating material and/or heat treated and/or machined in a manner similar to that described above.

Additionally, provisional application Ser. No. 60/642,449, filed Jan. 7, 2005 and entitled "Coated Artificial Implant Devices and Methods of Making and Using" with Z. Zhang et al. as inventors is hereby incorporated by reference. Further, the non-provisional application based upon this provisional application, that is, application Ser. No. 11/326,984, filed Jan. 6, 2006 is also hereby incorporated by reference.

Although the invention herein has been described with reference to particular embodiments, it is to be understood that these embodiments and modifications or variations are merely illustrative of the principles and applications of the present invention. It is therefore to be understood that numerous other modifications may be made to the illustrative embodiments and that other arrangements may be devised without departing from the spirit and scope of the present invention as defined by the appended claims.

What is claimed is:

1. A method of fabricating a medical implant component, said method comprising the steps of:
    producing a substrate from a first material, said substrate having a bearing portion;
    spraying particles of a second material onto the bearing portion of the substrate in accordance with a predetermined spraying technique to provide a coating thereon; and
    subjecting the coated bearing portion to a sintering process in a pressure controlled atmosphere, wherein in the sintering process a first pressure is maintained for a first portion of the sintering process and a second pressure is maintained for a second portion of the sintering process to obtain a predetermined inter-diffusion zone of the first material and the second material, the second pressure exceeding the first pressure and the first portion preceding the second portion in the sintering process,
    wherein, upon completion of the fabrication, the bearing portion is a bearing surface which is operable to articulate with a portion of a member or another medical implant component.

2. The method according to claim 1, wherein the first material is different from the second material.

3. The method according to claim 2, wherein said predetermined spraying technique is a thermal type spraying process.

4. The method according to claim 3, wherein said thermal type spraying technique is one of a plasma spraying process or a high velocity oxygen fuel (HVOF) spraying process.

5. The method according to claim 4, wherein the HVOF spraying process is a kerosene type spraying process.

6. The method according to claim 2, wherein the first material is a biocompatible metal or an alloy thereof.

7. The method according to claim 6, wherein the second material is a ceramic material.

8. The method according to claim 7, wherein the ceramic material is any one of an oxide, carbide, nitride, or nitrocarbide of any of the following elements: silicon (Si), titanium (Ti), tantalum (Ta), tungsten (W), zirconium (Zr), niobium (Nb), chromium (Cr), or aluminium (Al.

9. A method of fabricating a medical implant component, said method comprising the steps of:
    producing a substrate from a first material, said substrate having a bearing portion;
    spraying particles of a second material onto the bearing portion of the substrate in accordance with a predetermined spraying technique to provide a coating of the second material thereon having a first thickness;
    grinding the coating of the second material so that the coating has a second thickness which is less than the first thickness; and
    subjecting the coating of the second material after the coating has been ground to the second thickness to a sintering process in a pressure controlled atmosphere, wherein in the sintering process a first pressure is maintained for a first portion of the sintering process and a second pressure is maintained for a second portion of the sintering process to obtain a predetermined inter-diffusion zone of the first material and the second material, the second pressure exceeding the first pressure and the first portion preceding the second portion in the sintering process,
    wherein, upon completion of the fabrication, the bearing portion of said substrate having the coating of the second material is operable to articulate with a portion of a member or another medical implant component.

10. The method according to claim 9, further comprising the step of grinding the coating of the second material after being subjected to the sintering process in the pressure controlled atmosphere so that the coating has a third thickness which is less than the second thickness.

11. The method according to claim 10, wherein the first material is different from the second material.

12. The method according to claim 11, wherein said predetermined spraying technique is a thermal type spraying process.

13. The method according to claim 12, wherein said thermal type spraying technique is a plasma spraying process or a high velocity oxygen fuel (HVOF) spraying process.

14. The method according to claim 11, wherein the first material is a biocompatible metal or an alloy thereof.

15. The method according to claim 14, wherein the second material is a ceramic material.

16. The method according to claim 15, wherein the ceramic material is chromium oxide or chromium carbide.

17. The method according to claim 1, wherein the coating of the second material has a thickness of at least approximately 25 microns.

18. The method according to claim 1, wherein the first material is the same as the second material.

19. The method according to claim 1, wherein the medical implant component is a femoral ball head component.

20. The method according to claim 9, wherein the third thickness of the coating has a value of at least approximately 25 microns.

21. The method according to claim 9, wherein the first material is the same as the second material.

22. The method according to claim 9 wherein the medical implant component is a femoral ball head component.

23. The method according to claim 6, wherein the second material is a ceramic metal (cermet) composite material.

24. The method according to claim 23, wherein the cermet composite material is formed from any (i) oxide, carbide, nitride, or nitro-carbide of any of the following elements: Si, Ti, Ta, W, Zr, Nb, Cr, or Al, and (ii) any of Ti or an alloy thereof, cobalt chrome or an alloy thereof, Zr metal or an alloy thereof, Ta or an alloy thereof, or stainless steel.

25. The method according to claim 14, wherein the second material is a ceramic metal (cermet) composite material.

26. The method according to claim 25, wherein the cermet composite material is formed from any (i) oxide, carbide, nitride, or nitro-carbide of any of the following elements: Si, Ti, Ta, W, Zr, Nb, Cr, or Al, and (ii) any of Ti or an alloy thereof, cobalt chrome or an alloy thereof, Zr metal or an alloy thereof, Ta or an alloy thereof, or stainless steel.

27. The method according to claim 1, wherein the sintering process obtains in the second material a diffusion or chemical bond with the first material having a bond strength between about 7000-9000 psi.

28. The method according to claim 9, wherein the sintering process obtains in the second material a diffusion or chemical bond with the first material having a bond strength between about 7000-9000 psi.

* * * * *